United States Patent
Li et al.

(10) Patent No.: US 9,139,543 B2
(45) Date of Patent: Sep. 22, 2015

(54) THIAZOLE COMPOUNDS AND USES THEREOF

(71) Applicant: Institute of Pharmacology and Toxicology Academy of Military Medical Sciences P.L.A. China, Beijing (CN)

(72) Inventors: Song Li, Beijing (CN); Wu Zhong, Beijing (CN); Juan Liu, Beijing (CN); Kunlun He, Beijing (CN); Junhai Xiao, Beijing (CN); Xinbo Zhou, Beijing (CN)

(73) Assignee: Institute of Pharmacology and Toxicology Academy of Military Medical Sciences P.L.A. China, Beijing (CN)

( * ) Notice: Subject to any disclaimer, the term of this patent is extended or adjusted under 35 U.S.C. 154(b) by 0 days.

(21) Appl. No.: 14/399,680

(22) PCT Filed: May 10, 2013

(86) PCT No.: PCT/CN2013/075471
§ 371 (c)(1),
(2) Date: Nov. 7, 2014

(87) PCT Pub. No.: WO2013/166989
PCT Pub. Date: Nov. 14, 2013

(65) Prior Publication Data
US 2015/0119430 A1     Apr. 30, 2015

(30) Foreign Application Priority Data
May 11, 2012   (CN) .......................... 2012 1 0144906

(51) Int. Cl.
*C07D 277/42*     (2006.01)
(52) U.S. Cl.
CPC .................... *C07D 277/42* (2013.01)
(58) Field of Classification Search
None
See application file for complete search history.

(56) References Cited

U.S. PATENT DOCUMENTS 6,114,365 A     9/2000  Pevarello et al.

FOREIGN PATENT DOCUMENTS

| CN | 102241628 A | 11/2011 |
|---|---|---|
| CN | 102241673 A | 11/2011 |
| CN | 102336720 A | 2/2012 |
| WO | WO 00/26203 A1 | 5/2000 |
| WO | WO 2010/077068 A2 | 7/2010 |

OTHER PUBLICATIONS

Chemical Abstracts Registry No. 1429483-79-3, indexed in the Registry file on STN CAS Online Apr. 30, 2013.*
Chemical Abstracts Registry No. 1429483-78-2, indexed in the Registry file on STN CAS Online Apr. 30, 2013.*
Chemical Abstracts Registry No. 1429483-77-1, indexed in the Registry file on STN CAS Online Apr. 30, 2013.*
Chemical Abstracts Registry No. 1429483-76-0, indexed in the Registry file on STN CAS Online Apr. 30, 2013.*
Chemical Abstracts Registry No. 1429483-75-9, indexed in the Registry file on STN CAS Online Apr. 30, 2013.*
International Search Report (ISR) for PCT/CN2013/075471; I.A. fd: May 10, 2013, mailed Aug. 22, 2013 from the State Intellectual Property Office of the P.R. China, Beijing, China.
International Preliminary Report on Patentability (IPRP), Chapter I of the Patent Cooperation Treaty, including the Written Opinion for PCT/CN2013/075471; I.A. fd: May 10, 2013, issued Nov. 25, 2014, from the International Bureau of WIPO, Geneva, Switzerland.
Liu, J et al., "SAR, Cardiac Myocytes Protection Activity and 3D-QSAR Studies of Salubrinal and its Potent Derivatives," Current Medicinal Chemistry 19 (35):6072-6079, (Dec. 2012), Bentham Science Publishers, The Netherlands.

* cited by examiner

*Primary Examiner* — Laura L. Stockton
(74) *Attorney, Agent, or Firm* — Sterne, Kessler, Goldstein & Fox P.L.L.C.

(57) ABSTRACT

The present invention relates to a compound of Formula (I), or an isomer, pharmaceutically acceptable salt and solvate thereof; the present invention further relates to a pharmaceutical composition, which comprises the compound of Formula (I), or isomer, pharmaceutically acceptable salt or solvate thereof, and a pharmaceutically acceptable carrier, excipient or diluents; the present invention further relates to the use of the compound of Formula (I), or isomer, pharmaceutically acceptable salt or solvate thereof, for anti-apoptosis, prophylaxis or treatment of a disease or symptom associated with apoptosis, especially for protecting myocardial cells, and prophylaxis or treatment of a disease or symptom associated with cardiomyocyte apoptosis.

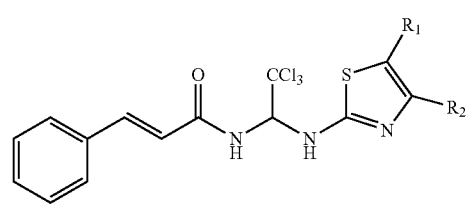

(I)

7 Claims, No Drawings

THIAZOLE COMPOUNDS AND USES THEREOF

TECHNICAL FIELD

The present invention relates to novel thiazole compounds and uses thereof in manufacture of a medicament for anti-apoptosis and a medicament for protection of myocardial cells.

BACKGROUND ART

Apoptosis refers to programmed cell death of body cells during development or under some factors, caused by regulation of intracellular genes and products thereof. Apoptosis universally exists in biosphere, occurs under either physiological state or pathological state, and plays an important role in embryo development, morphogenesis, stabilization of normal cells in tissues, defense and immune reaction of body, cell damage caused by diseases or intoxication, aging, occurrence and development of tumors. Thus it has been a hotspot for biomedical research.

Researches indicate that occurrence of many serious diseases relate to excessive apoptosis, for example, decreased of $CD4^+$ T cells number in development of AIDS; cell death mediated by cytotoxic T cells in graft rejection; apoptosis of myocardial cells and nerve cells in ischemia reperfusion injury; nerve system degradation diseases (e.g., Alzheimer's disease, Parkinson's disease, etc.); apoptosis of many tissue cells caused by exposing to ionizing radiation.

Some evidences show that cardiomyocyte apoptosis closely relates to occurrence, development and prognosis of many heart diseases. Researches of cardiomyocyte apoptosis show that myocardial death of infarct is not equivalent to myocardial necrosis, apoptosis is one of mechanisms of myocardial infarction, and is also main form of myocardial death in early stage of infarction and myocardial death caused by ischemia/reperfusion, and apoptosis of large amount of myocardial cells at this moment aggravate damage of cardiac muscle. In 1989, Nepomniashchikh, et al, found that in observation of ultra-structure of starved myocardial atrophy, structure protein synthesis of myocardial cells reduced, cell number decreased, but corresponding proportional decrease of cell nucleus was not accompanied, and thus it is primarily suggested that starved myocardial atrophy was caused by apoptosis. In 1994, Gottlieb and Kawano, et al, obtained direct evidence of cardiomyocyte apoptosis using electron microscope in combination with DNA gel electrophoresis, the former disclosed that reperfusion injury induced rabbit cardiomyocyte apoptosis, while the latter confirmed that myocarditis patients were accompanied with cardiomyocyte apoptosis. Tanaka, et al, also confirmed the existence of apoptosis in cultured myocardial cells of suckling mice. With the advance of methodology and intensive study of apoptosis, the pathological effects of cardiomyocyte apoptosis were found in many heart diseases. Studies showed that heart injury in spontaneous hypertension rats (SHR) was related to apoptosis; The conversion from hypertrophic heart in advanced stage to heart failure was caused by cardiomyocyte apoptosis; in acute myocardial infarction, besides necrosis, early infarction and reperfusion injury also induced apoptosis; cardiomyocyte apoptosis was also observed in transplanted heart and right ventricular dysplasia cardiomyopathy, and anoxia also induced cardiomyocyte apoptosis.

To some extents, apoptosis was reversible, cardiomyocyte apoptosis in myocardial infarction and ischemia/reperfusion has its features and rules, and these features could be used to prevent and reduce apoptosis to provide suggestions for clinical prevention of ischemia/reperfusion; during reperfusion procedure, apoptosis occurred in contraction band zone (around infarct focus) is induced by some causes, and thus inhibition factors of apoptosis, like medicament, could be used to prevent apoptosis and treat relative diseases caused by apoptosis.

However, medicament available in clinical for anti-apoptosis and cell protection is very few in sorts and quantity, and not effective in selectivity and targeting, so it is of great importance to develop new, safe and effective anti-apoptotic and cell-protective drugs, especially those with completely new mechanism of action.

CONTENTS OF THE INVENTION

In order to develop new, safe and effective anti-apoptotic and cell-protective drugs, the inventors found from long-term and massive experimental researches that a group of thiazole compounds have effects of anti-apoptosis and protecting myocardial cells, and can be used for prophylaxis or treatment of diseases or symptoms associated with cardiomyocyte apoptosis. Specifically, the first aspect of the present invention relates to a compound of general Formula (I), or an isomer, pharmaceutically acceptable salt and solvate thereof,

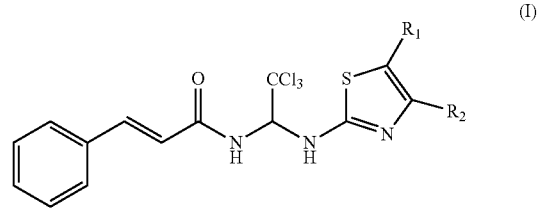

wherein $R_1$ represents hydrogen, alkyl, substituted alkyl, cycloalkyl, cycloalkyl-alkyl, phenyl, substituted phenyl, phenylalkyl, substituted phenylalkyl;

$R_2$ represents phenyl, substituted phenyl.

In the present invention, the substituted alkyl, substituted phenyl, substituted phenylalkyl respectively refers to alkyl, phenyl or phenylalkyl substituted with one or more (e.g., 2, 3) groups selected from the following: halogen, alkyl, alkoxy, cycloalkyl, hydroxy, nitro, cyano, sulfydryl.

In the present invention, the alkyl refers to $C_{1-8}$ alkyl, which means a straight or branched alkyl having 1-8 carbon atoms, for example, 1-6 carbon atoms, for example 1-4 carbon atoms, for example, methyl, ethyl, propyl, isopropyl, butyl, isobutyl, sec-butyl, tert-butyl, pentyl, 2-ethyl-butyl, hexyl, heptyl, octyl, etc.

In the present invention, the cyclo-alkyl refers to $C_{3-8}$ cycloalkyl, which means a cyclic alkyl having 3-8 carbon atoms. Examples of the cycloalkyl include cyclopropyl, cyclobutyl, cyclopentyl, cyclohexyl, cycloheptyl, and cyclooctyl, etc.

In the present invention, the cycloalkyl-alkyl refers to a cycloalkyl linked with an alkyl as side chain, the definitions of the cycloalkyl and alkyl are the same as the above mentioned, and examples of the cycloalkyl-alkyl could be cyclopenylmethyl, cyclohexylmethyl, cyclopenylethyl, cyclohexylethyl.

In the present invention, the phenylalkyl refers to that a phenyl linked with an alkyl as side chain, the definition of the alkyl is the same as the above mentioned, and examples of the phenylalkyl could be phenylmethyl, phenylethyl, phenylpropyl, etc.

In the present invention, the alkoxy refers to "alkyl-O—", in which alkyl is defined as the above mentioned.

In the present invention, the halogen refers to fluorine, chlorine, bromine, iodine.

The compound according to the first aspect of the present invention, or isomer, pharmaceutically acceptable salt and solvate thereof, in which:

$R_1$ represents hydrogen, methyl, propyl, hexyl, cyclopentylmethyl, cyclohexylmethyl, cyclopentylethyl, cyclohexylethyl, phenyl, 2-methoxyphenyl, 4-methoxyphenyl;

$R_2$ represents phenyl, 4-methoxyphenyl, 2-methoxyphenyl, 2-chlorophenyl, 4-chlorophenyl, 2,4-dichlorophenyl, 2,4-difluorophenyl.

Said compound according to the first aspect of the present invention, or isomer, pharmaceutically acceptable salt and solvate thereof, in which:

$R_1$ represents hydrogen, hexyl, cyclopentylmethyl, phenyl;

$R_2$ represents phenyl, 4-methoxyphenyl, 2,4-difluorophenyl, 4-chlorophenyl.

The compound according to the first aspect of the present invention, or isomer, pharmaceutically acceptable salt and solvate thereof, which is selected from the following compounds:

(1) (2E)-3-(2-phenyl)-N-{1-[4-(4-methoxyphenyl)-5-phenyl-2-thiazolyl]-2,2,2-trichlor oethyl}-2-acrylamide;

(2) (2E)-3-(2-phenyl)-N-[1-(4,5-diphenyl-2-thiazolyl)-2,2,2-trichloroethyl]-2-acrylamide;

(3) (2E)-3-(2-phenyl)-N-[1-(4-methoxyphenyl-2-thiazolyl)-2,2,2-trichloroethyl]-2-acrylamide;

(4) (2E)-3-(2-phenyl)-N-[1-(2,4-difluorophenyl-2-thiazolyl)-2,2,2-trichloroethyl]-2-acrylamide;

(5) (2E)-3-(2-phenyl)-N-[1-(4-chlorophenyl-2-thiazolyl)-2,2,2-trichloroethyl]-2-acrylamide;

(6) (2E)-3-(2-phenyl)-N-[1-(4-phenyl-2-thiazolyl)-2,2,2-trichloroethyl]-2-acrylamide;

(7) (2E)-3-(2-phenyl)-N-{1-[4-(4-methoxyphenyl)-5-cyclopentylmethyl-2-thiazolyl]-2,2,2-trichloroethyl}-2-acrylamide.

The compound according to the first aspect of the present invention can be prepared via the following method:

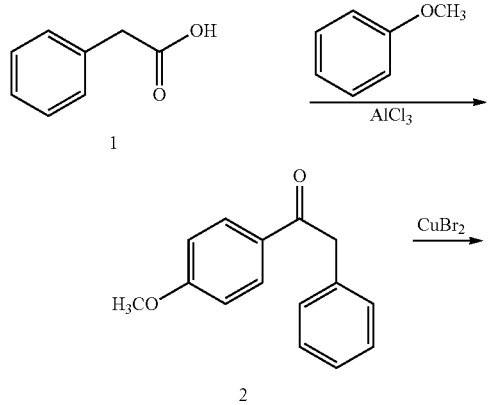

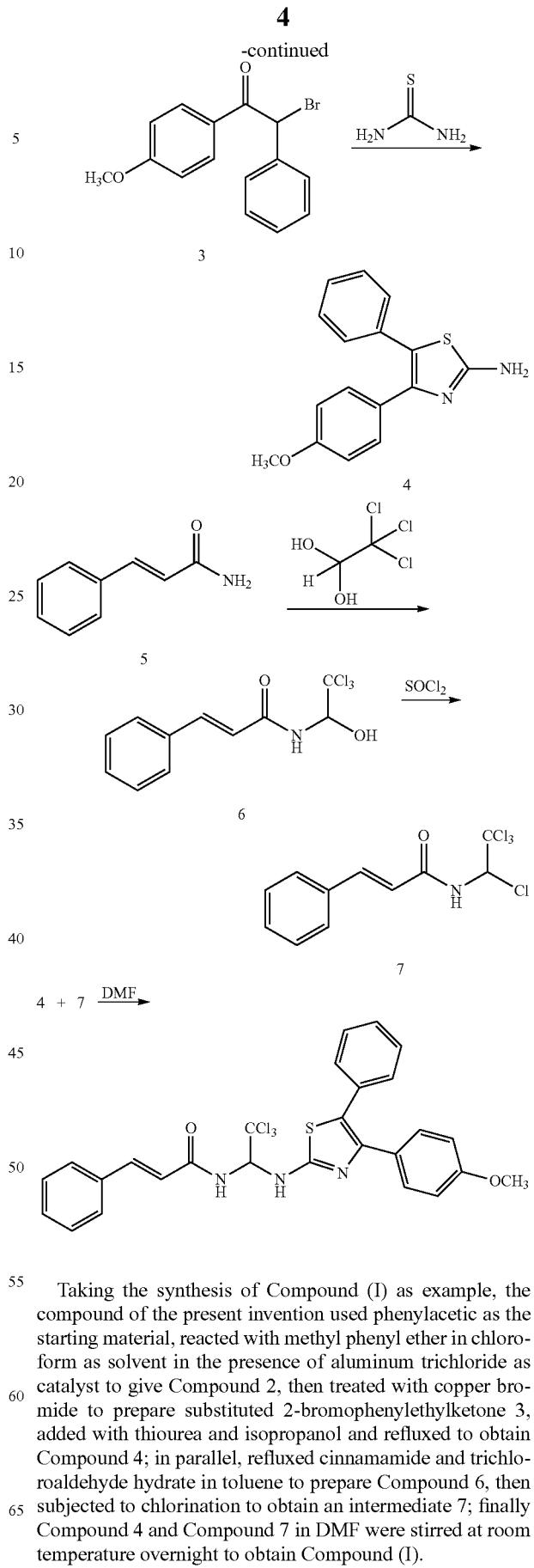

Taking the synthesis of Compound (I) as example, the compound of the present invention used phenylacetic as the starting material, reacted with methyl phenyl ether in chloroform as solvent in the presence of aluminum trichloride as catalyst to give Compound 2, then treated with copper bromide to prepare substituted 2-bromophenylethylketone 3, added with thiourea and isopropanol and refluxed to obtain Compound 4; in parallel, refluxed cinnamamide and trichloroaldehyde hydrate in toluene to prepare Compound 6, then subjected to chlorination to obtain an intermediate 7; finally Compound 4 and Compound 7 in DMF were stirred at room temperature overnight to obtain Compound (I).

The effects of anti-apoptosis and myocardial cells protecting of the compound of the present invention are shown in Examples.

Another aspect of the present invention relates to a pharmaceutical composition, which comprises the compound of the first aspect of the present invention, or isomer, pharmaceutically acceptable salt or solvate thereof, and a pharmaceutically acceptable carrier, excipient or diluents.

The present invention further relates to a use of the compound of Formula (I) of the first aspect of the present invention, or isomer, pharmaceutically acceptable salt or solvate thereof, in manufacture of a medicament for anti-apoptosis, prophylaxis or treatment of a disease or symptom associated with apoptosis.

The present invention further relates to a use of the compound of Formula (I) of the first aspect of the present invention, or isomer, pharmaceutically acceptable salt or solvate thereof, in manufacture of a medicament for protecting myocardial cells, prevention or treatment of a disease or symptom associated with cardiomyocyte apoptosis.

The present invention further relates to a method for anti-apoptosis, prevention or treatment of a disease or symptom associated with apoptosis, the method comprising administering to a subject in such need a therapeutically effective amount of the compound of Formula (I) of the first aspect of the present invention, or isomer, pharmaceutically acceptable salt or solvate thereof.

The present invention further relates to a method for protecting myocardial cells, prevention or treatment of a disease or symptom associated with cardiomyocyte apoptosis, the method comprising administering to a subject in such need a therapeutically effective amount of the compound of Formula (I) of the first aspect of the present invention, or isomer, pharmaceutically acceptable salt or solvate thereof.

The disease or symptom associated with apoptosis in the present invention includes but is not limited to cardiovascular diseases, nerve regressive diseases (e.g., Alzheimer disease, Parkinson's disease, etc.), multiple sclerosis, viral infection, AIDS, transplant rejection, ionizing radiation, etc.

The disease or symptom associated with cardiomyocyte apoptosis in the present invention includes but is not limited to (i) starved myocardial atrophy, (ii) myocarditis, (iii) heart failure, (iv) myocardial damage caused by primary hypertension, (v) myocardial damage caused by early acute myocardial infarction, (vi) myocardial damage caused by reperfusion in acute myocardial infarction, (vii) myocardial cytopathy caused by heart transplantation, (viii) dysplasia myocardial diseases; cardiomyocyte apoptosis caused by anoxia, or sclerosis of cardiovascular system.

Those skilled in the art should understand that the compound of Formula I has a chiral center. When a single enantiomer of the compound of Formula I is required, it can be prepared by using reactants present in single enantiomer form in any possible steps, or prepared by performing reaction in the presence of an reagent or catalyst in single enantiomer form, or prepared by resolution of a mixture of stereoisomers via conventional methods. Some preferable methods comprises resolution using microorganisms, resolution of diastereomer salt formed from any usable chiral acid, for example, mandelic acid, camphor-sulfonic acid, tartaric acid, lactic acid, etc., or resolution of diastereomer salt formed from chiral base, such as bracine, cinchona alkaloid or derivatives thereof. Commonly used methods can be seen in "Enantiomers, Racemates and Resolution" edited by Jaques et al (Wiley Interscience, 1981).

Those skilled in the art should be aware of the compound of the present invention can also be used in form of its pharmaceutically acceptable salt (physiologically acceptable salt) or solvate. The physiologically acceptable salt of the compound of Formula I includes conventional salts formed from pharmaceutically acceptable inorganic acid or organic acid or inorganic base or organic base and acid addition salt of quaternary ammonium. More specific examples of suitable acid salts include salts of hydrochloric acid, hydrobromic acid, sulfuric acid, phosphoric acid, nitric acid, perchloric acid, fumaric acid, acetic acid, propionic acid, succinic acid, hydroxyacetic acid, formic acid, lactic acid, maleic acid, tartaric acid, citric acid, pamoic acid, malonic acid, hydroxymaleic acid, phenylacetic acid, glutamic acid, benzoic acid, salicylic acid, fumaric acid, toluene sulfonic acid, methylsulfonic acid, naphthalene-2-sulfonic acid, benzene sulfonic acid, hydroxynaphthoic acid, hydroiodic acid, malic acid, steroic, tannic acid, etc. As for other acids, such as oxalic acid, although they per se are not pharmaceutically acceptable, they can be used for prepare salts as intermediates to obtain the compound of the present invention and pharmaceutically acceptable salts thereof. More specific suitable alkali salts include salts of sodium, lithium, potassium, magnesium, aluminum, calcium, zinc, N,N'-dibenzylethylenediamine, chloroprocaine, choline, diethanolamine, ethylenediamine, N-methylglucosamine, and procaine. The compound of the present invention as mentioned thereafter includes the compound of Formula I and pharmaceutically acceptable salt and solvate thereof.

The present invention further comprises a prodrug of the compound of the present invention, and once the prodrug is administered, it is chemically converted via metabolic procedure into an active drug. In general, this kind of prodrug is a functional derivative of the compound of the present invention, which can be readily converted into the needed compound of Formula (I) in vivo. For example, "Design Of Prodrugs", edited by H Bund Saard, Elsevier, 1985, describes conventional methods of selecting and preparing suitable prodrug derivatives.

The present invention also includes active metabolites of the compound of the present invention.

Another aspect of the present invention relates to a pharmaceutical composition, comprising a racemic or optical isomer of the compound of the present invention and at least one pharmaceutically acceptable carrier, and could be used in vivo treatment with biocompatibility. The pharmaceutical composition can be processed into various forms for different administration routes. The compound of the present invention can also be processed into various pharmaceutically acceptable salts.

The pharmaceutical composition of the present invention comprises an effective amount of the compound of Formula I of the present invention or a pharmaceutically acceptable salt or hydrate thereof and one or more suitable pharmaceutically acceptable carriers. The pharmaceutically acceptable carriers comprise but are not limited to: ion exchangers, alumina, aluminum stearate, lecithin, serum protein such as human albumin, buffering substance such as phosphate, glycerol, sorbic acid, potassium sorbate, mixture of partial glycerides of saturated plant fatty acids, water, salts or electrolytes, such as protamine sulfate, disodium hydrogen phosphate, potassium hydrogen phosphate, sodium chloride, zinc salt, colloid silica, magnesium trisilicate, polyvinylpyrrolidone, cellulose substances, polyethylene glycol, sodium carboxymethylcellulose, polyacrylates, beeswax, lanolin.

The pharmaceutical composition of the compound of the present invention can be administered in any of the following manners: oral administration, spray inhalation, rectal administration, nasal administration, bucca administration, topical administration, parenteral administration, such as subcutaneous, intravenous, intramuscular, intraperitoneal, intrathecal, intraventricular, intrasternal, intracranial injection or perfusion, or administration with aid of an explanted reservoir, preferably oral administration, intraperitoneal or intravenous administration.

In oral administration, the compound of the present invention can be processed in any acceptable forms for oral administration, including but not being limited to tablets, capsules, water solutions or water suspensions. The tablets use a carrier generally comprising lactose and maize starch, additionally comprising a lubricant such as magnesium stearate. The capsules use a diluent generally comprising lactose and dry maize starch. The water suspensions usually use a mixture of an active component and suitable emulsifying agent and suspending agent. If necessary, the above oral dosage forms can further comprise some sweetening agents, flavoring agents or coloring agents.

In topical administration, especially in treatment of neurogenic disease of a readily accessible affected surface or organ such as eye, skin or inferior part of intestinal tract by topical external application, the compound of the present invention can be processed into different dosage forms for topical administration according to different affected surfaces or organs, which are illustrated as follows:

In topical administration of eyes, the compound of the present invention can be processed in a dosage form of micronized suspension or solution, in which the used carrier is isotonic sterile saline with a certain pH, wherein a preservative such as chlorobenzylalkanol salt can be added or not. For the eye use, the compound can also be processed into ointment form, such as Vaseline ointment.

In topical administration of skin, the compound of the present invention can be processed in suitable dosage forms such as ointments, lotions or creams, wherein the active component is suspended or dissolved in one or more carriers. The carriers usable in ointments include but are not limited to: mineral oil, paraffin liquid, white vaseline, propylene glycol, polyethylene oxide, polypropylene oxide, emulsified wax and water; the carriers usable in lotions or creams include but are not limited to: mineral oil, sorbitan monostearate, Tween 60, hexadecane ester wax, hexadecylene aromatic alcohol, 2-octyldodecanol, benzyl alcohol and water.

The compound of the present invention also can be administered in dosage form of sterile injections, including water or oil suspensions for sterile injection, or sterile injection solutions. The usable carriers and solvents include water, Ringer's solution and isotonic sodium chloride solution. In addition, sterile nonvolatile oil can also be used as solvent or suspending medium, such as monoglyceride or diglyceride.

It should be further pointed out that the dose and usage method of the compound of the present invention depend on many factors, including age, body weight, gender, natural health status, nutritional status, activity of compound, administration time, metabolic rate, severity of disease and subjective judgment of doctor.

BENEFICIAL EFFECTS OF THE INVENTION

The present invention provides a thiazole compound, and demonstrates that it has the effects of anti-apoptosis and cell protecting, and thus provides a new method and approach for treatment of disease or symptom caused by apoptosis, especially for treatment of disease or symptom caused by cardiomyocyte apoptosis.

SPECIFIC MODELS FOR CARRYING OUT THE INVENTION

The embodiments of the present invention are illustrated as follows in combination with examples, but those skilled in the art would understand that the following examples are merely to illustrate the present invention and should not be deemed as restriction of the present invention. The examples which specific conditions are not given are performed according to conventional conditions or conditions suggested by manufacturers. The reagents or instruments which manufacturers are not given are all conventional products commercially available from markets.

Melting point of compound was measured by RY-1 Melting Point Apparatus, and thermometer was not calibrated. Mass spectrum was measured by Micromass ZabSpec High Resolution Mass Spectrometer (resolution: 1000). $^1$H NMR was measured by JNM-ECA-400 Superconductive NMR Instrument, working frequency: $^1$H NMR 400 MHz, $^{13}$C NMR 100 MHz.

EXAMPLES

Example 1

(2E)-3-(2-phenyl)-N-{1-[4-(4-methoxyphenyl)-5-phenyl-2-thiazolyl]-2,2,2-trichloroethyl}-2-acrylamide

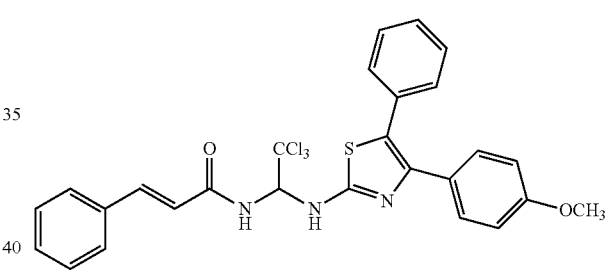

1.10 g of cinnamamide and 1.20 g of trichloroaldehyde hydrate were added to 30 ml of toluene and refluxed at 110° C. for 8 h, cooled to room temperature to precipitate a large amount of yellow lamellar crystal of (2E)-3-(2-thienyl)-N-(1-hydroxy-2,2,2-trichloroethyl)acrylamide (1.20 g). It was dissolved in 20 ml of anhydrous THF, DMF was added as catalyst, and 1.2 ml of SOCl$_2$ was added dropwise at room temperature, heated to 60° C. and reacted for 2 h. The solvent was evaporated to give a yellow solid of (2E)-3-(2-thienyl)-N-(1,2,2,2-tetrachloroethyl)acrylamide, which was washed with cool petroleum ether to neutral, and dried in vacuum for use. 1.44 g of phenylacetic acid was dissolved in 20 ml of THF, and 2.50 g of SOCl$_2$ was added dropwise at room temperature, refluxed for 2 h, rotary evaporated to remove the solvent to obtain a yellow oil. The yellow oil was dissolved in 10 ml of anhydrous chloroform, and slowly added dropwise under ice-bath to a solution of 1.06 g of methyl phenyl ether and 2.66 g of aluminum trichloride in 20 ml of chloroform, and reacted at room temperature for 2 h after the addition. The reaction solution turned from orange to dark brown. 20 ml of water was slowly added dropwise, the reaction solution was layered. The lower layer was washed with saturated brine for 3 times, 20 ml per time. The organic layer was rotary evaporated to obtain 4'-methoxy-2-phenyl-phenylethylketone. It was refluxed with 4.40 g of CuBr$_2$ in a mixture solvent of 10 ml of ethyl acetate and 10 ml of chloroform for 3 h, the black solid turned white, and the solution turned from clear to dark green. The solid was removed by filtration after the reaction The reaction solution was rotary evaporated and dissolved in 15 ml isopropanol, added with 0.76 g of thiourea, refluxed for 1.5 h, and a large amount of faint yellow solid was precipitated as 4-(4-methoxyphenyl)-5-phenyl-2-aminothiazole. It was added to 20 ml of DMF together with the above mentioned (2E)-3-(2-thienyl)-N-(1,2,2,2-tetrachloroethyl)acrylamide, and stirred at room temperature for 24 h. The reaction solution was poured into 40 ml of water, extracted with ethyl acetate for 3 times, 20 ml each, the organic phases were combined and washed with saturated brine for 3 times, 50 ml each. The organic phase was directly added with 4 g of crude silica gel and stirred, eluted with petroleum ether:ethyl acetate=4:1, to obtain 0.30 g of white solid.

$^1$H-NMR (400 MHz, DMSO-$d_6$) δ3.74 (s, 3H); δ6.84-6.86 (dd, 2H); 6.94-6.98 (m, 1H); δ7.26-7.46 (m, 6H); δ7.55-7.61 (t, 1H); δ8.71-8.73 (d, 1H); δ9.03-9.05 (d, 1H). MS (TOF) 559.5 (M+).

Example 2

(2E)-3-(2-phenyl)-N-[1-(4,5-diphenyl-2-thiazolyl)-2,2,2-trichloroethyl]-2-acrylamide

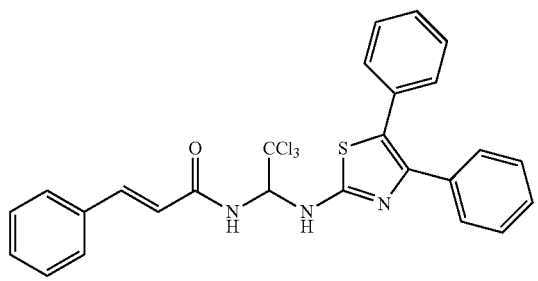

The method of Example 1 was used, in which methyl phenyl ether was replaced with benzene, to obtain 0.20 g of faint yellow solid.

$^1$H-NMR (400 MHz, DMSO-$d_6$) δ6.92-6.96 (d, 1H); δ6.97-7.10 (t, 1H); δ7.22-7.37 (m, 8H); δ7.38-7.43 (m, 5H); δ7.57-7.61 (m, 3H); δ8.83-8.86 (d, 1H); δ9.08-9.11 (d, 1H). MS (TOF) 529.4 (M+).

Example 3

(2E)-3-(2-phenyl)-N-[1-(4-methoxyphenyl-2-thiazolyl)-2,2,2-trichloroethyl]-2-acrylamide

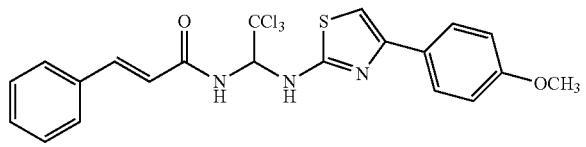

The method of Example 1 was used, in which phenylacetic acid was replaced with acetic acid, to obtain 0.20 mg of white solid.

$^1$H-NMR (400 MHz, DMSO-$d_6$) δ3.76 (s, 3H); δ6.91-6.95 (d, 1H);
δ6.96-7.00 (t, 1H); δ7.20 (s, 1H); δ7.34-7.39 (m, 5H); δ7.53-7.57 (m, 3H); δ7.83-7.85 (dd, 2H); δ8.65-8.67 (d, 1H); δ8.99-9.01 (d, 1H). MS (TOF) 483.4 (M+).

Example 4

(2E)-3-(2-phenyl)-N-[1-(2,4-difluorophenyl-2-thiazolyl)-2,2,2-trichloroethyl]-2-acrylamide

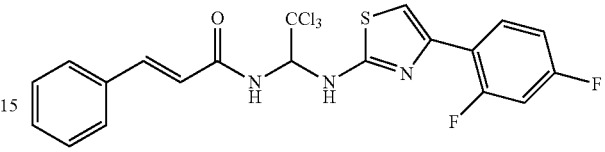

The method of Example 1 was used, in which phenylacetic acid was replaced with acetic acid, and methyl phenyl ether was replaced with 2,4-difluorobenzene, to obtain 0.23 g of white solid.

$^1$H-NMR (400 MHz, DMSO-$d_6$)
δ6.90-6.94 (d, 1H); δ6.96-6.99 (t, 1H); δ7.11-7.12 (d, 1H); δ7.20-7.24 (q, 1H); δ7.30-7.34 (q, 1H); δ7.39-7.45 (m, 3H); δ7.56-7.60 (m, 3H);
δ8.08-8.12 (m, 1H); δ8.76-8.79 (d, 1H); δ9.04-9.06 (d, 1H). MS (TOF) 448.0 (M+).

Example 5

(2E)-3-(2-phenyl)-N-[1-(4-chlorophenyl-2-thiazolyl)-2,2,2-trichloroethyl]-2-acrylamide

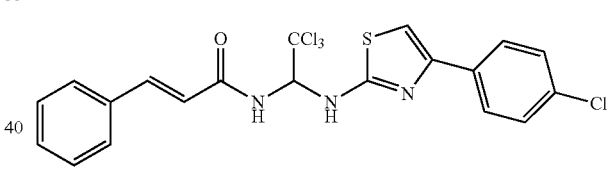

The method of Example 1 was used, in which phenylacetic acid was replaced with acetic acid, and methyl phenyl ether was replaced with 4-fluorobenzene, to obtain 0.12 g of white solid.

$^1$H-NMR (400 MHz, DMSO-$d_6$) δ6.91-6.95 (d, 1H); δ6.96-7.00 (d, 1H); δ7.30 (s, 1H); δ7.40-7.48 (m, 5H); δ7.55-7.60 (m, 3H); δ7.87-7.89 (m, 2H); δ8.73-8.75 (d, 1H); δ9.03-9.05 (d, 1H).
MS (TOF) 488.1 (M+).

Example 6

(2E)-3-(2-phenyl)-N-[1-(4-phenyl-2-thiazolyl)-2,2,2-trichloroethyl]-2-acrylamide

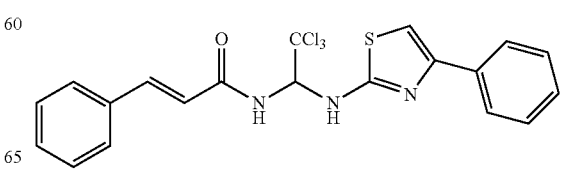

The method of Example 1 was used, in which phenylacetic acid was replaced with acetic acid, and methyl phenyl ether was replaced with benzene, to obtain 0.22 g of white solid.

$^1$H-NMR (400 MHz, DMSO-$d_6$) δ6.91-6.95 (d, 1H); δ6.96-7.00 (t, 1H); δ7.22 (s, 1H); δ7.28-7.30 (t, 1H); δ7.38-7.43 (m, 5H); δ7.55-7.59 (m, 3H); δ7.85-7.87 (dd, 2H); δ8.67-8.69 (d, 1H); δ9.01-9.03 (d, 1H). MS (TOF) 453.6 (M+).

Example 7

(2E)-3-(2-phenyl)-N-{1-[4-(4-methoxyphenyl)-5-cyclopentylmethyl-2-thiazolyl]-2,2,2-trichloroethyl}-2-acrylamide

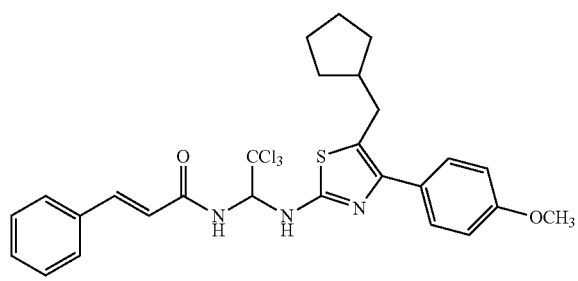

The method of Example 1 was used, in which phenylacetic acid was replaced with 3-cyclopentylpropanoic acid, to obtain 0.19 g of yellow solid.

$^1$H-NMR (400 MHz, DMSO-$d_6$) δ0.81-0.88 (t, 3H); δ1.04-1.07 (t, 1H); δ1.30-1.36 (m, 2H); δ1.50-1.56 (m, 2H); δ2.70-2.74 (t, 2H); δ3.16-3.17 (d, 1H); δ3.78 (s, 3H);

δ6.86-6.90 (t, 1H); δ6.92-6.96 (d, 1H);

δ6.97-6.99 (d, 1H); δ7.41-7.48 (m, 5H); δ7.53-7.60 (m, 3H); δ8.39-8.42 (d, 1H); δ8.92-8.94 (d, 1H). MS (TOF) 465.5 (M+).

Example 8

(2E)-3-(2-phenyl)-N-[1-(4-phenyl-2-thiazolyl)-2,2,2-trichloroethyl]-2-acrylamide hydrochloride

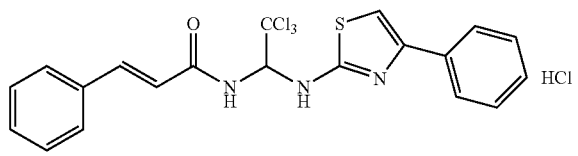

2 ml of hydrochloric acid ethyl acetate solution was added to 0.15 g of the compound of Example 6, stirred for 5 h to precipitate white solid, filtrated to obtain the target compound in amount of 0.12 g. The element analysis result was as follows: C, 49.05%; H, 3.46%; N, 8.59%.

Example 9

Evaluation of Effects of the Compound for Anti-Apoptosis and Protecting Myocardial Cells 1, Animals and Reagents Neonatal Wistar rats newborn within 24 h, not confined to female or male (provided by the Center of Laboratory Animals, Academy of Military Medical Science of the PLA, animal certificate No.: SCXK-(军) 2007-004). High-sugar DMEM culture medium, trypsinase, and type II collagenase purchased from Gibco Company; fetal bovine serum (FBS) purchased from Beijing Yuanhengshengma Biological Technology Institute; 5-bromo-2-deoxyuridine (5-Brdu), tunicamycin (TM) purchased from Sigma Company; thiazolyl blue (MTT), dimethyl sulfoxide (DMSO) which is the product of Amresco; other chemical agents were all analytical pure and made in China. Universal Microplate ReaderEL800 type of ELIASA was a product of BIO-TEK Company of US.

2, Primary Culture of Myocardial Cells neonatal Wistar rats newborn within 24 h were used, skin of abdomen was sterilized with iodine and alcohol. Tissue of ventricular apex was taken out with aseptic operation, cut into pieces with 1 mm$^3$ size, added with suitable amount of 0.125% pancretin and 0.1% collagenase II (final concentration was respectively 0.1% and 0.02%), mechanical shaking in 37° C. water-bath, 10 min each time, digested repeatedly until the tissue pieces were completely digested. The prepared myocardial cell suspension was inoculated in a 75 cm$^2$ culture flask. Non-myocardial cells were removed by differential adhesion method. The myocardial cell density was adjusted with DMEM culture medium containing 10% FBS, inoculated to a 96-well plate in an amount of 10$^4$/ml, placed in 5% CO$_2$ incubator at 37° C. for 24 h for primary culture. Half medium was replaced after 24 h, a culture medium containing 0.1% 5-Brdu (5-bromo-2-deoxyuridine) was replenished to inhibit the growth of non-myocardial cells. The medium was replaced once per 48 h for primary culture.

3, Measurement of Cell Survival Rate (MTT)

Measurement of compound toxicity: the compound of the present invention was formulated with DMSO, in which DMSO was solvent. Myocardial cells were cultured for 4 days, then respectively treated with compound in different concentrations (0 μM, 0.3 μM, 1 μM, 3 μM, 10 μM, 30 μM, 100 μM, 300 μM), placed in 37° C., 5% CO$_2$ incubator and cultured for 48 h, then each well was added with 10 μl of MTT (5 mg/ml) and incubated continuously for 4 h, finally each well was added with 100 μL of 10% SDS, and incubated at 37° C., 5% CO$_2$ for 24 h, so that MTT crystal was dissolved completely. ELISA was used to measure light absorbance of each well under 550 nm wavelength. The formula is: inhibition rate (%)=(OD value of administration group/average OD value of solvent control well)×100%, in which the solvent control group was DMSO. The dose-effect curve was drawn by using logarithm of compound concentration as horizontal coordinate and average of compound inhibition rate as vertical coordinate, and half-cells inhibition dose (IC50) was calculated with Origin analysis software. The results were expressed in x̄±SD, and the compound concentration with cytotoxicity could be preliminarily determined by this method.

4, Activity of Preventing Cardiomyocyte Apoptosis Induced by Tm

Measurement of compound activity: myocardial cells were cultured for 4 days, respectively treated with compound in different concentrations (0.3 μM, 1 μM, 3 μM) for 30 min, then added with TM to final concentration of 0.5 μg/ml (TM group with final concentration of 0.5 μg/ml and solvent control group (DMSO) were set at the same time), and placed in 37° C., 5% CO$_2$ incubator and cultured for 48 h, then each well was added with 10 μl of MTT (5 mg/ml) and continuously incubated for 4 h, finally each well was added with 100 μL of 10% SDS, incubated at 37° C., 5% CO$_2$ for 24 h, so that MTT crystal was completely dissolved. ELISA was used to measure light absorbance of each well under 550 nm wavelength, in which TM and the compound of the present invention were formulated with DMSO. The formula is: cell survival rate (%)=OD value of administration group/average OD value of solvent control well×100%. The results were expressed in x̄±SD, and EC50 values (Table 1) were calculated with software, so that the effect of compound of the present invention preventing cardiomyocyte apoptosis induced by TM was determined.

The results of activity of experimental compound in protecting myocardial cells were shown as follows:

TABLE 1

Protection effects against cardiomyocyte apoptosis induced by TM

| Compound | EC50 (uM) |
|---|---|
| Example 1 | 100 |
| Example 2 | 47 |
| Example 3 | 61 |
| Example 4 | 0.8 |
| Example 5 | 0.3 |
| Example 6 | 30 |

The experimental results showed that the compounds of Example 4 and 5 had good protection effects against cardiomyocyte apoptosis induced by TM.

Although the specific models for carrying out the invention have been described in details, those skilled in the art would understand that according to the disclosed teachings, these details could be subjected to various modifications and replacements, and all of these alternations are covered by the protection scope of the present invention. The protection scope of the present invention is determined by the attached claims and any equivalents thereof.

What is claimed is:

1. A compound of Formula (I), or an isomer, pharmaceutically acceptable salt and solvate thereof,

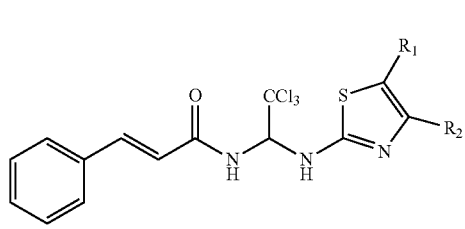

(I)

wherein
$R_1$ represents hydrogen, alkyl, substituted alkyl, cycloalkyl, cycloalkyl-alkyl, phenyl, substituted phenyl, phenylalkyl, or substituted phenylalkyl; and
$R_2$ represents phenyl or substituted phenyl.

2. The compound according to claim 1, or isomer, pharmaceutically acceptable salt and solvate thereof, wherein
$R_1$ represents hydrogen, methyl, propyl, hexyl, cyclopentylmethyl, cyclohexylmethyl, cyclopentylethyl, cyclohexylethyl, phenyl, 2-methoxyphenyl, or 4-methoxyphenyl; and $R_2$ represents phenyl, 4-methoxyphenyl, 2-methoxyphenyl, 2-chlorophenyl, 4-chlorophenyl, 2,4-dichlorophenyl, or 2,4-difluorophenyl.

3. The compound according to claim 2, or isomer, pharmaceutically acceptable salt and solvate thereof, wherein
$R_1$ represents hydrogen, hexyl, cyclopentylmethyl, or phenyl; and
$R_2$ represents phenyl, 4-methoxyphenyl, 2,4-difluorophenyl, or 4-chlorophenyl.

4. The compound according to claim 3, or isomer, pharmaceutically acceptable salt and solvate thereof, which is selected from the following compounds:
(1)(2E)-3-(2-phenyl)-N-{1-[4-(4-methoxyphenyl)-5-phenyl-2-thiazolyl]-2,2,2-trichloroethyl}-2-acrylamide;
(2)(2E)-3-(2-phenyl)-N-[1-(4,5-diphenyl-2-thiazolyl)-2,2,2-trichloroethyl]-2-acrylamide;
(3)(2E)-3-(2-phenyl)-N-[1-(4-methoxyphenyl-2-thiazolyl)-2,2,2-trichloroethyl]-2-acrylamide;
(4)(2E)-3-(2-phenyl)-N-[1-(2,4-difluorophenyl-2-thiazolyl)-2,2,2-trichloroethyl]-2-acrylamide;
(5)(2E)-3-(2-phenyl)-N-[1-(4-chlorophenyl-2-thiazolyl)-2,2,2-trichloroethyl]-2-acrylamide;
(6)(2E)-3-(2-phenyl)-N-[1-(4-phenyl-2-thiazolyl)-2,2,2-trichloroethyl]-2-acrylamide; and
(7)(2E)-3-(2-phenyl)-N-{1-[4-(4-methoxyphenyl)-5-cyclopentylmethyl-2-thiazolyl]-2,2,2-trichloroethyl-2-acrylamide.

5. A pharmaceutical composition, which comprises the compound of any one of claims 1-4, or isomer, pharmaceutically acceptable salt or solvate thereof, and a pharmaceutically acceptable carrier, excipient or diluents.

6. A method for anti-apoptosis treatment of a disease or symptom associated with apoptosis, the method comprising administering to a subject in such need a therapeutically effective amount of the compound of any one of claims 1-4, or isomer, pharmaceutically acceptable salt or solvate thereof, wherein the disease or symptom associated with apoptosis is selected from the group consisting of Alzheimer's disease, Parkinson's disease, multiple sclerosis, AIDS, transplant rejection, and ionizing radiation.

7. A method for protecting myocardial cells or treatment of a disease or symptom associated with cardiomyocyte apoptosis, the method comprising administering to a subject in such need a therapeutically effective amount of the compound of any one of claims 1-4, or isomer, pharmaceutically acceptable salt or solvate thereof, wherein the disease or symptom associated with cardiomyocyte apoptosis is selected from the group consisting of (i) starved myocardial atrophy, (ii) myocarditis, (iii) heart failure, (iv) myocardial damage caused by primary hypertension, (v) myocardial damage caused by early acute myocardial infarction, (vi) myocardial damage caused by reperfusion in acute myocardial infarction, (vii) myocardial cytopathy caused by heart transplantation, (viii) dysplasia myocardial diseases; and cardiomyocyte apoptosis caused by anoxia, or sclerosis of cardiovascular system.

* * * * *